US010369183B2

(12) United States Patent
Stennett et al.

(10) Patent No.: US 10,369,183 B2
(45) Date of Patent: Aug. 6, 2019

(54) THERAPEUTIC COMPOSITIONS FROM JAMAICAN BITTER YAM AND METHODS OF MAKING AND USING SAME

(75) Inventors: Dewayne K. Stennett, Montego Bay (JM); Helen N. Asemota, Kingston (JM)

(73) Assignee: University of The West Indies, Kingston (JM)

( * ) Notice: Subject to any disclaimer, the term of this patent is extended or adjusted under 35 U.S.C. 154(b) by 347 days.

(21) Appl. No.: 12/533,143

(22) Filed: Jul. 31, 2009

(65) Prior Publication Data
US 2010/0143509 A1    Jun. 10, 2010

Related U.S. Application Data

(60) Provisional application No. 61/085,652, filed on Aug. 1, 2008.

(51) Int. Cl.
*A61K 36/8945* (2006.01)
*A23L 33/105* (2016.01)

(52) U.S. Cl.
CPC ........ *A61K 36/8945* (2013.01); *A23L 33/105* (2016.08); *A23V 2002/00* (2013.01)

(58) Field of Classification Search
None
See application file for complete search history.

(56) References Cited

FOREIGN PATENT DOCUMENTS

WO    WO 9506417 A1 *  3/1995

OTHER PUBLICATIONS

Riley et al. In vitro Digestibility of Raw Starches Extracted from five Yam(*Dioscorea* spp.) Species Grown in Jamaica:. Starch/Stärke, vol. 56 (2004) 69-73.*
McAnuff et al. "Proximate Analysis and Some Antinutritional Factor Constituents in Selected Varieties of Jamaican Yams (*Dioscorea* and *Rajana* spp.)". Plant Foods for Human Nutrition, vol. 60 (2005) 93-98.*
Riley et al. Starch/Stärke (2004), 56. pp. 69-73.*
Riley et al. Starch/Stärke (2006), 58. pp. 418-424.*
McAnuff et all. West Indian Med J 2005; 54 (2): 97-100. (Year: 2005).*
Remington's. "Remington's Pharmaceutical Science 17th Edition". Gannaro, A (Ed.). pp. 1492 and 1516-1517. (Year: 1985).*
Bull, et al., "Acid Phosphatases", Mol. Pathol., 55:65-72 (2000).
Giugliano, et al., "Diabetes Mellitus, Hypertension, and Cardiovascular Disease: Which Role for Oxidative Stress?", Metabolism, 44:363-368 (1995).
Kakkar, et al., "Lipid Peroxidation and Activity of Antioxidant Enzymes in Diabetic Rats", Mol. Cell Biochem., 151:113-119 (1995).
Kurowska, et al., "Hypolipidemic Effects and Absorption of Citrus Polymethozylated Flavones in Hamsters with Diet-Induced Hypercholesterolemia", Journal of Agricultureal and Food Chemistry, 52:2879-2886 (2004).
McAnuff, et al., "Hpeatic Function Enzymes and Lipid Peroxidation in Streptozotocin-Induced Diabetic Rats Fed Bitter Yam (*Dioscorea polygonoides*) Steroidal Sapogenin Extract", Diabetologia Croatica, 32(1):17-23 (2003).
McAnuff, et al., "Hypoglycemic Effects of Steroidal Sapogenins Isolated from Jamaican Bitter Yam, *Diosorea Polytgonoides*", Food and Chemical Toxicology, 43:1667-1672 (2005).
Morris, et al., J. Agric Food Chem, 6:856-858 (1958).
Ozdemirler, et al., "Peroxidation Potential and Antioxidant Activity of Serum in Patients with Diabetes Mellitus and Myocardial Infarction", Horm Metab Res, 27:194-196 (1995).
Tan, et al., "Pioglitazone Reduces Atherogenic Index of Plasma in Patients with Type 2 Diabetes", Clinical Chemistry, 50(7):1184-1188 (2004).
Whitehead, et al., "A Prospective Study of the Causes of Notably Raised Aspartate Aminotransferases of Liver Origin", Gut, 45:129-133 (1999).
Eka, O.U. "The Chemical Composition of Yam Tubers." *Advances in Yam Research: The Biochemistry and Technology of the Yam Tuber*. Biochemical Society of Nigeria in Collaboration with Anambra State University of Technology. 1985. Al-United Industries & Shipping Inc. Taipei, Taiwan and Enugu, NIgeria. 30 pages.
Ogbuagu, M.N. "Nutritive and Anti-Nutritive Composition of the Wild (Inedible) Species of *Dioscorea bulbifera* (Potato Yam) and *Dioscorea dumentorum* (BItter Yam)." *The Pacific Journal of Science and Technology*. vol. 9, No. 1. May-Jun. 2008. 5 pages.
Okeke, CU et al. "Antioxidant Profile of Dioscorea Rotundata, Manihot Esculenta, Ipoemea Batatas, Vernonia Amygdalina and Aloe Vera." *Journal of Medical Research and Technology*. vol. 4, No. 1, Jun. 2007. 10 pages.
Okwu, D.E. et al. "Evaluation of the Phytonutrients, Mineral and Vitamin Contents of Some Varieties of Yam (*Dioscorea* sp.)." *International Journal of Molecular Medicine and Advance Sciences*. 2 (2): 199-203. 2006. 5 pages.
Poornima, G.N. et al. "Evaluation of Phytonutrients and Vitamin Contents in a Wild Yam, *Dioscorea belophylla* (Prain) Haines." *African Journal of Biotechnolgy*. vol. 8 (6), pp. 971-973. Mar. 20, 2009. 3 pages.
Afiukwa, et al., "Nutritional and Antinutritional Characterization of Two Wild Yam Species from Abakaliki, Southeast Nigeria", Research Journal of Pharmaceutical, Biological and Chemical Sciences, 4(2):840-848, Apr.-Jun. 2013, 9 pages.
Babiker, et al., "Effect of Reconstitution of $Na_2Co_3$ on Tannin Content and in vitro Protein Digestibility of Faba Bean Cultivars", Plant Foods for Human Nutrition, 44:119-130, Sep. 1993, 12 pages.
Barbehenn, et al., "Tannins in Plant-Herbivore Interactions", Phytochemistry, 72:1551-1565, Available online Feb. 26, 2011, 15 pages.

(Continued)

*Primary Examiner* — Amy L Clark
(74) *Attorney, Agent, or Firm* — Wilmer Cutler Pickering Hale and Dorr LLP

(57) ABSTRACT

The invention relates to therapeutic compositions, in particular to therapeutic compositions made from Jamaican bitter yam that are substantially free of tannins and alkaloids and comprise fiber, and methods of making and using such therapeutic compositions.

14 Claims, 8 Drawing Sheets

(56) References Cited

OTHER PUBLICATIONS

Lucas, et al., "Evaluation of Condensed Tannin Content of Some Native Tropical Tanniniferous Plants from Semi-Arid Regions in Brazil", Advances in Animal Biosciences, 1(1):273, Apr. 2010, retrieved from http://journals.cambridge.org/data/firstAbstract/ABS/ABS1_01/S2040470010004164a_abstract.jpg[Nov. 17, 2014 9:11:05 AM], 1 page.

McAnuff, "Analyses of Some Natural Products in Yams (*Dioscorea* spp.) and the Effect of Consumption of Bitter Yam (*D. polygonoides*) Steroidal Sapogenin Extract on Lipid Metabolism in Streptozotocin-Induced Diabetic Rats", Thesis Abstract, Dec. 16, 2008, University of the West Indies, retrieved from http://uwispace.sta.uwi.edu/dspace/handle/2139/2788, Oct. 2, 2014, 7 pages.

Noh, et al., "A New Approach to the Analysis of Tannin Concentration Using a Microelectronic Biosensor", Food Sci. Biotechnol., 22(1):201-205, Feb. 28, 2013, 5 pages.

Olayiwola, et al., "Study of Sweet Potato (*Ipomea batatas lam*) Foods for Indigenous Consumption Through Chemical and Anti-Nutritive Analysis in Kwara State, Nigeria", Pakistan Journal of Nutrition, 8(12):1894-1897, no Month Given, 2009, 4 pages.

Sedghi, et al., "Relationship Between Color and Tannin Content in Sorghum Grain: Application of Image Analysis and Artificial Neural Network", Brazilian Journal of Poultry Science, 14(1):57-62, Jan.-Mar. 2012, 6 pages.

Shajeela, et al., "Nutritional and Antinutritional Evaluation of Wild Yam", Tropical and Subtropical Agroecosystems, 14(2):723-730, May-Aug. 2011, 8 pages.

\* cited by examiner

SERUM TRIGLYCERIDE AND TOTAL, HDL, LDL AND VLDL CHOLESTEROL
LEVELS IN RAT MODEL OF DIABETES

THERAPEUTIC COMPOSITIONS FROM JAMAICAN BITTER YAM AND METHODS OF MAKING AND USING SAME

1. REFERENCE TO RELATED APPLICATION

This application claims the benefit of priority to U.S. Provisional Patent Application No. 61/085,652 filed Aug. 1, 2008, the entire disclosure of which is incorporated by reference herein.

2. FIELD OF THE INVENTION

The present invention generally relates to treatment of diabetes and hypercholesterolemia, and specifically to treatment of diabetes and hypercholesterolemia using compositions derived from plants.

3. BACKGROUND OF THE INVENTION

Diabetes mellitus is a clinical syndrome characterized by hyperglycemia due to insulin deficiency. It is by far the most common of the endocrine disorders and poses a serious challenge to health care worldwide. It is projected that by 2010, at least 239 million people will be affected by the disease (Thomas Mandrup-Poulsen, Clinical Review, Recent Advances, Diabetes, *BMJ* 316: 1221-25 (1998)). In Jamaica, the point prevalence of diabetes mellitus in the and over age group is estimated to be 17.9% (D. Ragoobirsingh et al., The Jamaican Diabetes Survey; A protocol for the Caribbean, *Diabetes Care* 18: 1277-79 (1995)), while in the United Kingdom, it is believed to be 2.4% of the adult population. In United States, diabetes ranks sixth as the primary cause of death, and has an estimated economic cost of between $85 billion and $92 billion, two thirds of which is a result of lost productivity because of hospitalizations or death (Jonathan C. Javitt and Yen-Pin Chiang, Economic Impact of Diabetes, in *Diabetes in America*, Ronald Aubert ed., pg. 601 (1995)). It is therefore clear that diabetes poses a threat to developing as well as developed countries.

Uncontrolled diabetes may result in the death of the patient or the development of complications of diabetes. Some of the characteristic long-term complications of diabetes are retinopathy with potential loss of vision, risk of developing atherosclerosis as well as peripheral vascular and cerebrovascular disease, nephropathy that may lead to renal failure, peripheral neuropathy with risk of developing foot ulcers and possible amputation.

Some of the most effective agents currently used to treat diabetes include synthetic substances such as sulfonylureas, biguanides, thiazolidinediones, meglitinides, α-glucosidase inhibitors and lipase inhibitors. These agents have various side effects such as renal and hepatic impairment, hematological disturbances, cholestatic jaundice, lactic acidosis, anemia and headaches. There remains a need for anti-diabetic products that do not cause such side effects.

Oxidative stress is believed to be a major contributor to cardiovascular disease in individuals having diabetes mellitus (see Giugliano et al. (1995), "Diabetes mellitus, hypertension, and cardiovascular disease: which role for oxidative stress?," *Metabolism* 44:363-368). It is well documented that diabetes is associated with increased oxidative stress, as evidenced by the increased accumulation of lipid peroxides in the plasma of diabetic rats (Kakkar et al. (1995), "Lipid peroxidation and activity of antioxidant enzymes in diabetic rats," *Mol Cell Biochem,* 151:113-119) and humans (Ozdemirler et al. (1995), "Peroxidation potential and antioxidant activity of serum in patients with diabetes mellitus and myocardial infarction," *Horm Metab Res* 27:194-196). There remains a need for medicines that reduce oxidative stress and kidney damage in diabetic patients.

Familial hypercholesterolemia affects approximately 1 in 500 people worldwide, and the elevated serum cholesterol concentrations associated with it is responsible for more than 50% of the risk of fatal or non-fatal coronary heart disease by age 50 in men, and for at least 30% of the risk in women aged 60 and above. The prevalence of hypercholesterolemia in Jamaica is estimated at 31%. It is estimated that 37.13%, or 101 million people in the United States suffer from hypercholesterolemia.

The major conventional drugs used to treat hypercholesterolemia include the statins (Lovastatin, Pravastatin, Simvastatin, etc.) and Niacin (Nicotinic acid). Although these drugs are effective in lowering serum cholesterol levels, they result in several adverse effects. Statins, for example, result in gastrointestinal upset, muscle aches, and hepatitis. Rarer problems are myopathy (defined as muscle pain with serum creatine kinase concentrations of more than 1000 U per liter), rash, peripheral neuropathy, and insomnia. Niacin also results in adverse effects including flushing, abdominal pain, vomiting, headache, or elevated serum aminotransferase levels indicating liver damage. There remains a need for medicines that reduce total and LDL cholesterol levels in diabetic patients without such side effects.

Citation of any reference in section 3 of this application is not an admission that the reference is prior art.

4. SUMMARY OF THE INVENTION

The invention is based, in part, on the discovery that a therapeutic product made from the Jamaican Bitter Yam is more effective than Jamaican Bitter Yam itself and more effective than its sapogenin extract in reducing indices of diabetes, without the undesirable side effects of existing anti-diabetic synthetic substances.

The invention is based, in part, on the discovery that a therapeutic product made from the Jamaican Bitter Yam is more effective than Jamaican Bitter Yam itself and more effective than its sapogenin extract in reducing total cholesterol levels, reducing LDL cholesterol levels, and increasing HDL cholesterol levels, without the undesirable side effects of existing anti-hypercholesterolemic synthetic substances.

In one aspect, the invention provides a therapeutic composition made from Jamaican bitter yam that is substantially free of tannins and alkaloids and comprises fiber. In some embodiments, the composition is substantially free of Jamaican bitter yam peel. In some embodiments, the composition contains less than about 0.1% tannins by weight. In some embodiments, the composition contains less than about 0.1% alkaloids by weight.

In another aspect, the invention provides a method for making a therapeutic composition from Jamaican bitter yam comprising: (a) providing Jamaican bitter yam; (b) pulverizing the Jamaican bitter yam into a powder; and (c) removing tannins and alkaloids from the powder to provide a substantially tannin-free and substantially alkaloid-free composition.

In some embodiments, the method further comprises drying the Jamaican bitter yam prior to pulverizing it. In some embodiments, the method further comprises removing the peel from the Jamaican bitter yam prior to drying it. In one embodiment, the tannins in the powder are removed by soaking the powder in a basic solution, e.g., sodium carbonate, sodium hydroxide, or potassium hydroxide. In one embodiment, the alkaloids in the powder are removed by chromatographic separation.

In yet another aspect, the invention provides a method for making a therapeutic composition from Jamaican bitter yam comprising: (a) providing Jamaican bitter yam; (b) drying and grinding the Jamaican bitter yam into a powder; (c) removing tannins from the powder by soaking the powder in a basic solution and removing the filtrate to provide a substantially tannin-free residue; (d) soaking the substantially tannin-free residue in a solvent to provide a substantially tannin-free solution; (e) removing any solid components from the solution; (f) removing alkaloids from the solution by chromatographic separation to provide a substantially alkaloid-free and substantially tannin-free solution; (g) removing the solvent from the substantially alkaloid-free and substantially tannin-free solution to provide a substantially alkaloid-free and substantially tannin-free solid; and (h) combining the substantially alkaloid-free and substantially tannin-free solid with the solid components from step (e) to provide a therapeutic composition. In one embodiment, the solvent is methanol.

In another aspect, the invention provides a method for treating diabetes comprising administering an effective amount of a therapeutic composition described herein to a subject in need thereof.

In yet another aspect, the invention provides a method for decreasing the blood glucose level in a subject comprising administering to the subject in need thereof an effective amount of a therapeutic composition of the invention, wherein the decrease of blood glucose level is observed relative to the subject prior to administration of the composition.

In one aspect, the invention provides a method for decreasing oxidative stress in a diabetic subject comprising administering to the subject in need thereof an effective amount of a therapeutic composition of the invention, wherein the decrease in oxidative stress is observed relative to the subject prior to administration of the composition.

In another aspect, the invention provides a method for decreasing liver damage in a diabetic subject comprising administering to the subject in need thereof an effective amount of a therapeutic composition of the invention, wherein the decrease in liver damage is observed relative to the subject prior to administration of the composition.

In one aspect, the invention provides a method for reducing LDL cholesterol level in a subject comprising administering to the subject in need thereof an effective amount of a therapeutic composition of the invention, wherein the reduction of LDL cholesterol level is observed relative to the subject prior to administration of the composition.

In another aspect, the invention provides a method for reducing total cholesterol level in a subject comprising administering to the subject in need thereof an effective amount of a therapeutic composition of the invention, wherein the reduction of total cholesterol level is observed relative to the subject prior to administration of the composition.

In still another aspect, the invention provides a method for increasing HDL cholesterol level in a subject comprising administering to the subject in need thereof an effective amount of a therapeutic composition of the invention, wherein the increase in HDL cholesterol level is observed relative to the subject prior to administration of the composition.

In one or more embodiments, the subject has diabetes mellitus.

In one or mode embodiments, the subject is a human.

5. BRIEF DESCRIPTION OF THE DRAWINGS

The invention is described with reference to the following figures, which are presented for purposes of illustration only and which are not intending to be limiting of the invention.

6. DETAILED DESCRIPTION OF THE INVENTION

6.1 Definitions and Abbreviations

Figure 1:
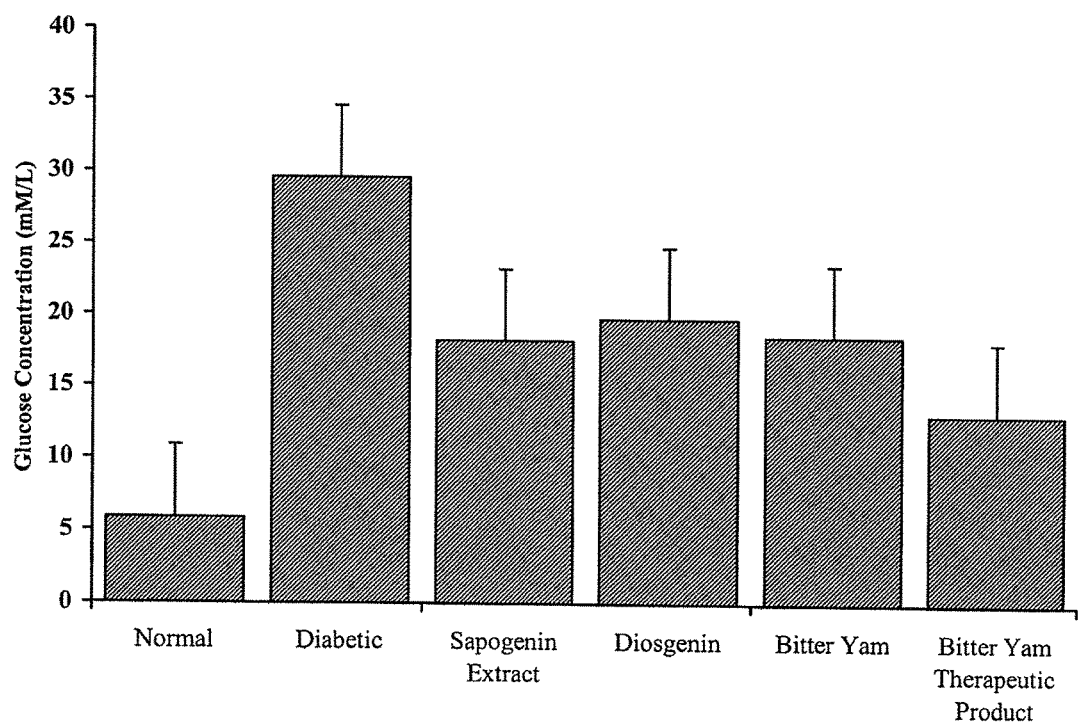
FIG. 1 is an illustration of the blood glucose levels in diabetic rats fed diet supplemented with Jamaican bitter yam therapeutic product (BYTP) and in control groups.

The following definitions are used herein:

A "sapogenin" refers to a non-sugar portion of a saponin that is typically obtained by hydrolysis, has either a complex terpenoid or a steroid structure and in the latter case forms a practicable starting point in the synthesis of steroid hormones. These compounds are frequently found in tubers. Illustrative sapogenins include, but are not limited to diosgenin, $\Delta$-3,5-diosgenin, stigmasterol, $\beta$-sitosterol, and pennogenin.

"Jamaican bitter yam therapeutic product", "BYTP", refers to a product made from Jamaican bitter yam (*Dioscorea polygonoides*) that is substantially free of tannins and alkaloids and comprises fiber.

An "alkaloid" is naturally occurring organic compound containing a basic nitrogen atom, which may have a bitter taste. Alkaloids include, but are not limited to, pyridine group alkaloids (e.g., piperine, coniine, trigonelline, arecaidine, guvacine, pilocarpine, cytisine, nicotine, sparteine, pelletierine); pyrrolidine group alkaloids: (e.g., hygrine, cuscohygrine, nicotine); tropane group alkaloids: (e.g., atropine, cocaine, ecgonine, scopolamine, catuabine); quinoline group alkaloids (e.g., quinine, quinidine, dihydroquinine, dihydroquinidine, strychnine, brucine, veratrine, cevadine); isoquinoline group alkaloids (e.g., the opium alkaloids (morphine, codeine, thebaine, isopapa-dimethoxy-aniline, papaverine, narcotine, sanguinarine, narceine, hydrastine, berberine), emetine, berbamine, oxyacanthine); phenethylamine group alkaloids (e.g., mescaline, ephedrine, dopamine, amphetamine); indole group alkaloids: tryptamines (e.g., DMT, N-methyltryptamine, psilocybin, serotonin), ergolines (e.g., the ergot alkaloids (ergine, ergotamine, lysergic acid, LSD)), beta-carbolines (e.g., harmine, harmaline, yohimbine, reserpine) and rauwolfia alkaloids (e.g., reserpine); purine group alkaloids: xanthines (e.g., caffeine, theobromine, theophylline); terpenoid group alkaloids: aconite alkaloids (e.g., aconitine) and steroids (e.g., solanine, samandaris (quaternary ammonium compounds) such as muscarine, choline, neurine); vinca alkaloids (e.g., vinblastine, vincristine); and other alkaloids (e.g., capsaicin, cynarin, phytolaccine, phytolaccotoxin).

A "tannin" is an astringent, bitter plant polyphenol that binds and precipitates a protein. Tannins can be divided into hydrolysable tannins and proanthocyanidins (also referred to as condensed tannins). Hydrolysable tannins are molecules with a polyol (generally D-glucose) as a central core. The hydroxyl groups of these carbohydrates can be partially or totally esterified with phenolic groups like gallic acid (gallotannins) or ellagic acid (ellagitannins). Hydrolysable tannins can also be classified into taragallotannins, having gallic acid) and quinic acid as the core, and caffetannins, having caffeic acid and quinic acid as a core. Proanthocyanidins are oligomers or polymers of flavonoid units (i.e., flavan-3-ol) linked by carbon-carbon bonds not susceptible to cleavage by hydrolysis. Examples include, but are not limited to, anthocyanidins such as cyanidin and delphinidin.

"Substantially free of [a substance]" means having less than 0.1% by weight (w/w) of the substance.

"About" means ±10% of the value that follows it.

The following abbreviations are used herein and have the indicated definitions:

LDL is low-density lipoprotein, HDL is high-density lipoprotein, VLDL is very-low-density lipoprotein, SEM is standard error of the mean, TBARS is thiobarbituric acid reactive substances, $R_f$ is retention factor, Hyp is hypercholesterolemic, AI is atherogenic index, TLC is thin layer chromatography, DMSO is dimethyl sulfoxide, PNP is p-nitrophenol, pyr is pyruvate, DMT is N,N-dimethyl-tryptamine.

6.2 Jamaican Bitter Yam

Jamaican bitter yam is an angiosperm, or flowering plant, that belongs to the Dioscoreaceae family within the order Dioscoreales. The Jamaican bitter yam species is *Dioscorea polygonoides*. Jamaican bitter yam grows in the hilly areas of Jamaica. Due to its bitter nature, it is currently underutilized because people consider it unpalatable. It has been shown that the consumption of Jamaican bitter yam is effective against hyperglycemia by reducing the indices of diabetes. (See McAnuff et al., Hypoglycemic effects of steroidal sapogenins isolated from Jamaican bitter yam, *Dioscorea polygonoides*, Food and Chemical Toxicology 43: 1667-1672 (2005)). Jamaican bitter yam has been shown to contain high levels of sapogenins, which have been proven to be effective against hyperglycemia and diabetes.

Specifically, Jamaican bitter yam contains at least the following three sapogenins: Δ-3,5-diosgenin, diosgenin, and pennogenin. It has also been shown that consumption of sapogenins extract from Jamaican bitter yam results in lower blood glucose levels in diabetic rats. (See McAnuff et al., 2005) Furthermore, it has been shown that in diabetic rats, consumption of Jamaican bitter yam sapogenin extract results in lower blood glucose levels than consumption of commercially available diosgenin. It has also been shown that consumption of Jamaican bitter yam itself is quite effective in reducing the indices of diabetes.

6.3 Methods of Making Jamaican Bitter Yam Therapeutic Product (BYTP)

The Jamaican bitter yam therapeutic product (BYTP) can, but does not need to be, in a form that is suitable for direct administration to a patient. Thus, the BYTP can also be considered as an active ingredient for preparation of therapeutic pharmaceutical compositions or nutraceuticals.

The Jamaican bitter yam therapeutic product can be made by the following process. First, one or more Jamaican bitter yam tubers are washed and peeled, leaving the inner yellow fleshy portion. The peeled tuber is then diced into small pieces and placed in a drying oven set to relatively low temperature of about 35° C. to 45° C. until dried. The dry pieces are then ground to a fine powder using a mill. To remove a significant portion of the tannins in the powder, the powder is then soaked in diluted sodium carbonate at room temperature for 24 hours. Alternatively, diluted sodium hydroxide or potassium hydroxide can be used instead of sodium carbonate. The soaked sample is then filtered, and the residue is washed with distilled water to remove any residual solvent. The residue is soaked in a methanol and water solution and filtered. The filtrate is then passed through a column of silica gel, and a number of fractions are collected. The presence of alkaloids in the resulting fractions is determined using thin layer chromatography. The fractions containing alkaloids are passed through the column of silica gel for a second time, and smaller fractions are collected. The resulting alkaloid-free fractions are combined, neutralized, and added to the residue from the prior filtration. The solution is mixed thoroughly, and the resulting mixture is dried at a low temperature and remilled into powder to form the resulting Jamaican bitter yam therapeutic product (BYTP).

6.4 Methods of Using the Jamaican Bitter Yam Therapeutic Product

In accordance with the invention, the Jamaican bitter yam product can be administered to a subject in need of treatment of diabetes.

6.4.1 Methods of Treating Diabetes

The Jamaican bitter yam therapeutic product is useful for treatment of diabetes. Accordingly, the invention provides methods for treating diabetes in a subject, comprising administering to a subject in need of such treatment an effective amount of Jamaican bitter yam therapeutic product.

In one embodiment, the subject in need of treatment of diabetes is considered to be at risk for the onset of diabetes. Examples of types of diabetes include, but are not limited to, type 1 diabetes mellitus, type 2 diabetes mellitus, and gestational diabetes. In another embodiment, the subject in need of treatment of diabetes has already experienced the onset of diabetes.

6.4.2 Methods of Decreasing Blood Glucose Levels

The invention provides methods for decreasing the blood glucose level in a subject, comprising administering to a subject in need of such treatment an effective amount of Jamaican bitter yam therapeutic product. In one embodiment, the subject in need of treatment suffers from hyperglycemia. Hyperglycemia can be chronic hyperglycemia.

6.4.3 Methods of Decreasing Oxidative Stress

The invention provides methods for decreasing oxidative stress in a subject, comprising administering to a subject in need of such treatment an effective amount of Jamaican bitter yam therapeutic product. Decrease in oxidative stress is observed/measured relative to the subject before administration of the Jamaican bitter yam therapeutic product.

6.4.4 Methods of Decreasing Liver Damage Associated with Diabetes

The invention provides methods for decreasing liver damage associated with diabetes in a subject, comprising administering to a subject in need of such treatment an effective amount of Jamaican bitter yam therapeutic product. Decrease in liver damage is observed/measured relative to the subject before administration of the Jamaican bitter yam therapeutic product.

Alanine and aspartate transaminase activities are used as an indicator of hepatocyte damage (see Whitehead et al. (1999), *Gut* 45:129-133). Acid phosphatase activity higher in diseased states than in normal states can be used as a tool in clinical investigations (Bull Murray et al. (2000), *Mol Pathol* 55:65-72).

6.4.5 Methods of Reducing Total Cholesterol Levels

The invention provides methods for reducing total cholesterol levels in a subject, comprising administering to a subject in need of such treatment an effective amount of Jamaican bitter yam therapeutic product. Reduction in total cholesterol level is observed/measured relative to the subject before administration of the Jamaican bitter yam therapeutic product. The subject can be a diabetic patient.

6.4.6 Methods of Reducing LDL Cholesterol Levels

The invention provides methods for reducing LDL cholesterol levels in a subject, comprising administering to a subject in need of such treatment an effective amount of Jamaican bitter yam therapeutic product. Reduction in LDL cholesterol level is observed/measured relative to the subject before administration of the Jamaican bitter yam therapeutic product. The subject can be a diabetic patient.

6.4.7 Methods of Increasing HDL Cholesterol Levels

The invention provides methods for increasing HDL cholesterol levels in a subject, comprising administering to a subject in need of such treatment an effective amount of Jamaican bitter yam therapeutic product. Increase in HDL cholesterol level is observed/measured relative to the subject before administration of the Jamaican bitter yam therapeutic product. The subject can be a diabetic patient.

6.4.8 Methods of Administering the Jamaican Bitter Yam Product

The Jamaican bitter yam product can be administered orally to a subject, for example in the form of a tablet. Generally, such tablet can comprise Jamaican bitter yam therapeutic product, in appropriate quantities, as well as other biomaterials from other food crops and prepared into tablet forms. The tablet may be swallowed or chewed by the subject. Because the product is substantially free of tannins, there is no unpleasant or bitter taste experienced by the subject when ingesting or chewing such a tablet, thus improving patient compliance.

In addition, the Jamaican bitter yam therapeutic product can be administered to a subject by mixing it with food or drink that is consumed by the subject. Because the product is substantially free of tannins, the food or drink consumed will not become bitter or have an unpleasant taste due to the addition of the product, thus improving patient compliance.

Of course, the Jamaican bitter yam therapeutic product can be formulated into pharmaceutical compositions together with pharmaceutically acceptable carriers for oral administration in solid or liquid form, or for intravenous, intramuscular, subcutaneous, transdermal, or topical administration.

Pharmaceutically acceptable carriers for oral administration include capsules, tablets, pills, powders, troches, and granules. In the case of solid dosage forms, the carrier can comprise at least one inert diluent such as sucrose, lactose, or starch. Such carriers can also comprise additional substances other than diluents, e.g., lubricating agents such as magnesium stearate. In the case of capsules, tablets, troches and pills, the carrier can also comprise buffering agents. Carriers, such as tablets, pills and granules, can be prepared with enteric coatings on the surfaces of the tablets, pills or granules. Alternatively, the enteric coated compounds can be pressed into tablets, pills, or granules. Pharmaceutically acceptable carriers include liquid dosage forms for oral administration, e.g., emulsions, solutions, suspensions, syrups and elixirs containing inert diluents commonly used in the art, such as water. Besides such inert diluents, compositions can also include adjuvants, such as wetting agents, emulsifying and suspending agents, and sweetening, flavoring agents.

Dosage forms for the topical or transdermal administration of a product according to the invention include powders, sprays, ointments, pastes, creams, lotions, gels, solutions, patches and inhalants. The product can be mixed under sterile conditions with a pharmaceutically acceptable carrier, and with any preservatives, buffers, or propellants which may be required.

Pharmaceutically acceptable carriers for topical administration include DMSO, alcohol or propylene glycol and the like that can be employed with patches or other liquid retaining material to hold the medicament in place on the skin. Approaches based on nanoparticles, nanoencapsulates and the like are also useful for the protection of the active principle and its slow release in the organism or specific tissues.

Pharmaceutical compositions of the invention for parenteral administration comprise product according to the invention in combination with one or more pharmaceutically acceptable sterile isotonic aqueous or non-aqueous solutions, dispersions, suspensions or emulsions, or sterile powders which can be reconstituted into sterile injectable solutions or dispersions just prior to use, which may contain antioxidants, buffers, bacteriostats, solutes which render the formulation isotonic with the blood of the intended recipient or suspending or thickening agents. Pharmaceutically acceptable carriers for intravenous administration include solutions containing pharmaceutically acceptable salts or sugars. Pharmaceutically acceptable carriers for intramuscular or subcutaneous injection include salts, oils, or sugars.

When used in its acid form, a product of the present invention can be employed in the form of a pharmaceutically acceptable salt of the acid. Carriers such as solvents, water, buffers, alkanols, cyclodextrins and aralkanols can be used. Other auxiliary, non-toxic agents can be included, for example, polyethylene glycols or wetting agents.

The pharmaceutically acceptable carriers and compositions of the invention are formulated into unit dosage forms for administration to the patients. The dosage levels of active ingredient (i.e., the Jamaican bitter yam therapeutic product) in the unit dosage can be varied so as to obtain an amount of active ingredient that is effective to achieve a therapeutic effect in accordance with the desired method of administration. The selected dosage level therefore mainly depends upon the nature of the active ingredient, the route of administration, and the desired duration of treatment. If desired, the unit dosage can be such that the daily requirement for the Jamaican bitter yam therapeutic product is in one dose, or divided among multiple doses for administration, e.g., two, three or four times per day.

This invention is further illustrated by the following examples, which should not be construed as limiting. Those skilled in the art will recognize, or be able to ascertain, using no more than routine experimentation, numerous equivalents to the specific substances and procedures described herein. A number of references have been cited, the entire disclosures of which have been incorporated herein in their entirety.

7. EXAMPLES

7.1 Example 1

Preparation of Jamaican Bitter Yam Therapeutic Product (BYTP)

Jamaican bitter yam, *Dioscorea polygonoides*, was harvested. The tubers were thoroughly washed and peeled, leaving the inner yellow fleshy portion. The peeled tuber was then diced into small pieces and placed in a drying oven set to relatively low temperature of about 35° C. to 45° C. for approximately forty-eight (48) hours. The dry pieces were then ground to a fine powder using a mill. The powder was then soaked in 20 times the volume of 0.05 M sodium carbonate (0.05 M NaOH or KOH can also be used) at room temperature for 24 hours to remove the tannins. The soaked sample was filtered, and the filtrate was discarded. The residue was washed three times with distilled water to remove any residual solvent. The residue was then soaked in about 2 liters of 50% methanol for 12 hours with constant stirring, and then filtered. The filtrate was evaporated to half of the volume, and 3-4% sodium hydroxide was added to adjust the pH to 10. The residue was stored at 4° C.

The neutralized filtrate was then passed through a column of silica gel (60 g/hL) and 50 ml fractions were collected. The presence of alkaloids in the fractions was determined using thin layer chromatography (TLC) and reference standards. The TLC plates were pre-coated with Silica gel G (Merck) with a 0.25 mm thickness. Development was carried out with different solvent systems—ethyl acetate:methanol:water (100:13.5:10 by volume), ethyl acetate:formic acid:acetic acid:water (100:11:11:27 by volume), chloroform:methanol:water (64:50:10 by volume), benzene:ethyl acetate (86:14 by volume), and ethyl acetate:methanol:water:acetic acid (65:15:15:10 by volume). After development in the solvents, the plates were dried in an oven at 80° C., sprayed with Dragendorrf's reagent, and visualized under UV light. The fractions containing alkaloids were subsequently passed through the column again, and smaller 10 ml fractions were collected. The presence of alkaloids in the smaller fractions was determined using the same TLC method as described above. All fractions containing alkaloids were discarded.

The alkaloid-free fractions were combined, neutralized to pH 7.0 using dilute acids such as acetic acid, added to the residue from the prior filtration, and mixed thoroughly. The resulting mixture was dried at a low temperature to a constant weight and remilled into powder.

Table 1 illustrates the composition of the Jamaican bitter yam therapeutic product compared to the composition of fresh Jamaican bitter yam ground into powder.

TABLE 1

| Components | Levels (g/kg dry weight) in Fresh bitter yam powder | Levels (g/kg dry weight) in Jamaican bitter yam therapeutic product |
|---|---|---|
| Protein | 51.70 ± 0.70 | 50.50 ± 0.80 |
| Ash | 15.70 ± 0.40 | 13.70 ± 0.30 |
| Fiber | 50.40 ± 7.00 | 48.30 ± 6.00 |
| Carbohydrate | 797.30 ± 8.90 | 680.30 ± 8.00 |
| Fat | 1.10 ± 0.20 | 1.10 ± 0.20 |
| Saponins | 2.96 ± 0.06 | 2.54 ± 0.12 |
| Total Phenols | 2.10 ± 0.20 | 2.00 ± 0.20 |
| Alkaloids | 7.82 ± 0.34 | 0.02 ± 0.00 |
| Total Condensed Tannin | 1.70 ± 0.10 | 0.10 ± 0.05 |
| Cyanoglucoside | (0.0008 ± 0.0001) | Not detected |
| Lectin | 3.00 ± 0.00 | 2.70 ± 0.01 |

Table 2 shows $R_f$ values and melting points of the different types of saponins found in the Jamaican bitter yam therapeutic product.

TABLE 2

| Saponins | $R_f$ Value | Melting Point (° C.) |
|---|---|---|
| Δ-3,5-diosgenin | 0.62 | 202-204 |
| stigmasterol and β-sitosterol | 0.40 | 134-140 |
| diosgenin | 0.30 | 205-207 |
| pennogenin | 0.20 | 219-221 |

The presence of saponins in the Jamaican bitter yam therapeutic product was confirmed using $^{13}C$ NMR spectroscopy, mass spectroscopy, and IR spectroscopy.

7.2 Example 2

Effects of Jamaican Bitter Yam Therapeutic Product on Indices of Diabetes

7.2.0 General Experimental Considerations

Experiments were carried out to test the metabolic effects of the Jamaican bitter yam therapeutic product (referred to in the illustrations and figures as BYTP) in rat and mice models of diabetes and hypercholesterolemia.

Experimental design for the animal studies: adult Wistar rats (40) were divided into six groups (8 rats per group, average body weight 249.0±0.3 g) as follows: Group 1—healthy rats receiving normal diet (normal); Group 2—diabetic rats fed normal diet (diabetic); Group 3—diabetic rats fed sapogenin extract (as 1% of the diet); Group 4—diabetic rats fed diosgenin (as 1% of normal diet); Group 5—diabetic rats fed bitter yam (as 1% of diet); and Group 6 fed the bitter yam therapeutic product (BYTP—as 1% of the diet).

Sapogenin extract was prepared from Jamaican bitter yam by the method of Morris et al. (1958), *J Agric Food Chem* 6:856-858. The sapogenin extract contained about 80% diosgenin, with the remaining 20% being made of β-sitosterol, pennogenin, stigmasterol, and $\Delta^2$ diosgenin.

The rats except the control group were made diabetic using standard procedures involving streptozotocin (60 mg/kg body weight in 0.05 M citrate buffer, pH 4.5) injection intraperitoneally. The control group rats were injected with an equivalent amount of buffer (0.05 M citrate buffer, pH 4.5). The normal rat diet (PMI Feeds Inc., Lab diet #5001) was a marketed laboratory rodent diet recommended for rats, mice and hamsters with the approximate chemical composition: protein 23%, fat 4.5%, fiber 6.0%, ash 8.0% and carbohydrate 58.5%. Rats were housed in stainless steel cages in a room kept on a 12-hour light-dark cycle, and were allowed to have access to their respective diets and water freely. The cages were cleaned daily. Body weight change, faecal output and total food intake were recorded weekly. The rats were fed on their respective diets for 4 weeks and sacrificed by decapitation after an overnight fast. Blood was collected in oxalate/fluoride vacutainers. The intestine, kidney, liver and spleen were excised, weighed and frozen in liquid nitrogen and stored at −20° C. until required for analysis. A section of the jejunum was cut and stored in 10% buffered formalin.

7.2.1. Effect of Administration of BYTP on Blood Glucose Levels of Diabetic Rats Glucose levels in blood plasma were determined using the method of Teller, J. D., Direct colometric determination of serum and plasma glucose, Abstracts of papers, 130th Meeting, American Chemical Society, Washington, D.C., 1956; 69C. As shown in FIG. 1, the induction of diabetes resulted in a significant increase in blood glucose compared to the normal group (see FIG. 1, columns 1 and 2). Supplementation of rat diets with bitter yam and bitter yam therapeutic product (BYTP) resulted in a significant decrease in blood glucose level compared to the diabetic control group. The greatest reduction of blood glucose was observed in the group fed a diet supplemented with the bitter yam therapeutic product. The data show that the BYTP is more effective in reducing blood glucose levels than the Jamaican bitter yam itself (see FIG. 1, columns 5 and 6).

7.2.2. Effect of Administration of BYTP on Blood Lipid Profile of Diabetic Rats Liver lipids were extracted with chloroform/methanol (2:1) according to the methods of Bligh and Dyer, *Can J Biochem Physiol*, 37: 911-917 (1959). Total cholesterol level was determined according to Zlatkis et al., *J Lab Clin Med*, 41: 486-492 (1953). HDL cholesterol level was determined using the method of Lopes-Virella et al., *Clin Chem*, 23: 882-885 (1977). The level of triglycerides was determined using the assay of Gottfried and Rosenberg, *Clin Chem*, 19: 1077-1078 (1973).

Figure 2:
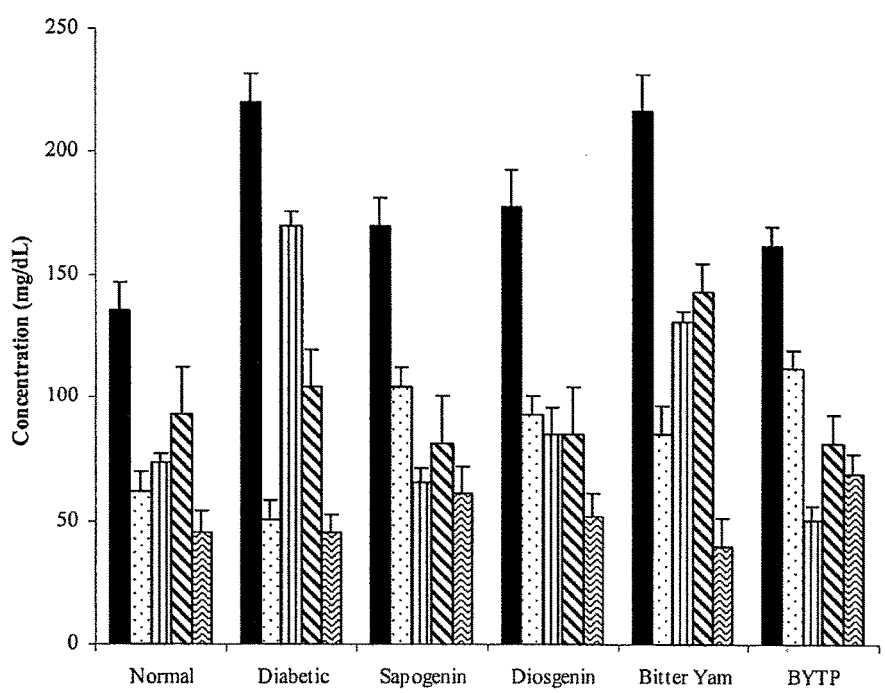
FIG. 2 is an illustration of the blood lipid profile in diabetic rats fed diet supplemented with Jamaican bitter yam therapeutic product (BYTP) and in control groups.

For diabetic rats, supplementation of diet with BYTP resulted in significant reductions in total cholesterol, VLDL-cholesterol, LDL-cholesterol and triglyceride levels in the serum (see FIG. 2). Additionally, the levels of HDL cholesterol (the "good" cholesterol) were increased by a diet supplemented with BYTP. Surprisingly, supplementation of the diet of diabetic rats with BYTP resulted in the greatest decrease in total cholesterol level, greatest increase of HDL cholesterol (the "good" cholesterol"), and the greatest decrease in VLDL and LDL cholesterol, thus indicating that BYTP has favorable anti-diabetic properties compared to sapogenin extract, diosgenin, and the Jamaican bitter yam (see FIG. 2).

Figure 3:
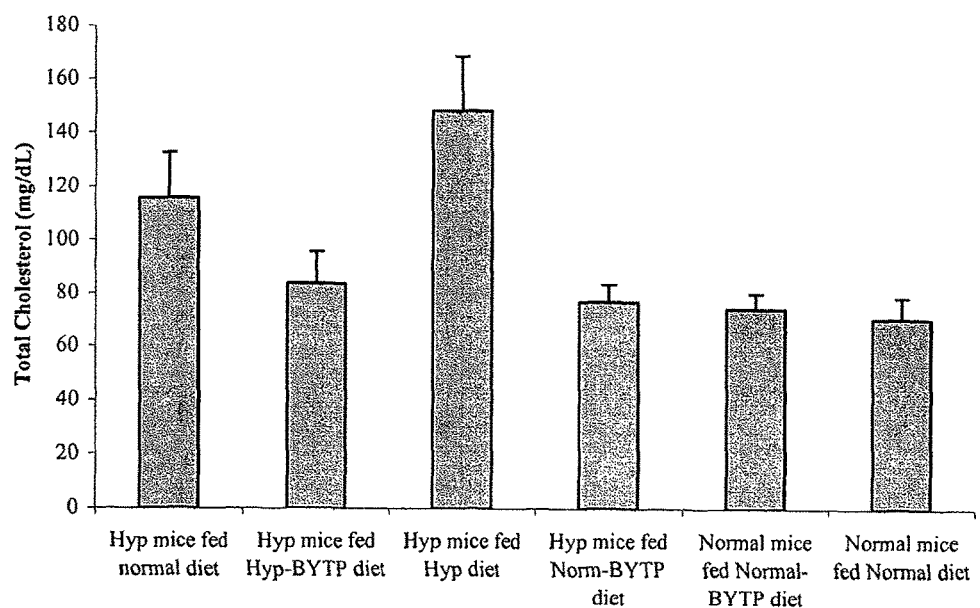
FIG. 3 is an illustration of the total cholesterol levels in hypercholesterolemic mice fed Jamaican bitter yam therapeutic product (BYTP) and in control groups.
Figure 4:
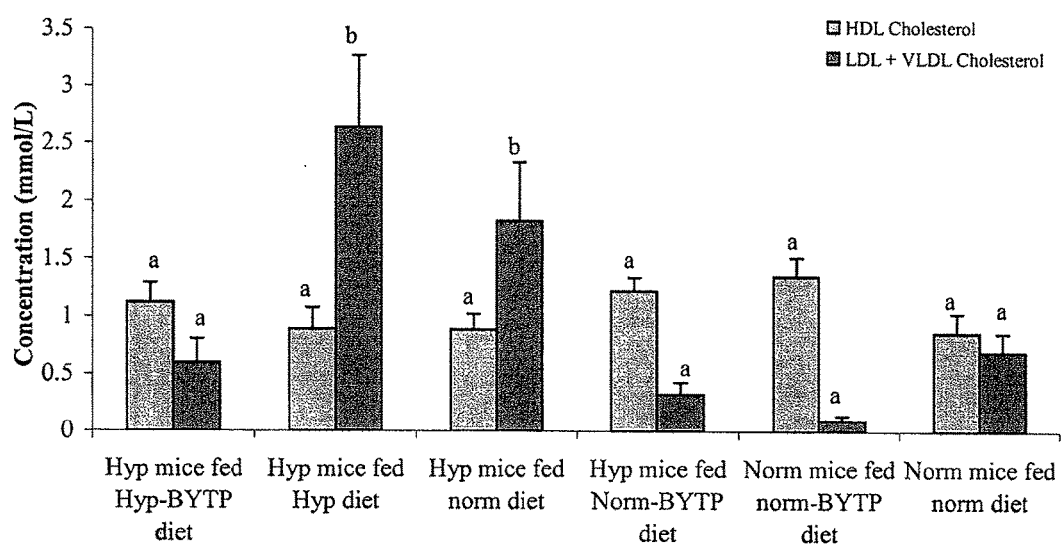
FIG. 4 is an illustration of the HDL, LDL and VLDL cholesterol levels in hypercholesterolemic mice fed Jamaican bitter yam therapeutic product (BYTP) and in control groups.

7.2.3. Effect of Administration of BYTP on Blood Lipid Profile of Hypercholesterolemic Mice In a similar study carried out using hypercholesterolemic (Hyp) mice, similar beneficial effects of BYTP on cholesterol levels were observed as in diabetic rats. FIGS. 3 and 4 show total, HDL, LDL and VLDL cholesterol levels in the serum of the hypercholesterolemic mice fed normal or hypercholesterolemic diet, with or without supplementation with the BYTP. Supplementation of the diets of hypercholesterolemic mice with the BYTP resulted in significant reductions in total cholesterol, VLDL and LDL cholesterol, while the levels of HDL cholesterol (i.e., the good cholesterol) were increased.

7.2.4. Effect of Administration of BYTP on Atherogenic Index for Hypercholesterolemic Mice Atherogenic Index (IP) can be calculated as ([total cholesterol]−[HDL cholesterol])/[HDL cholesterol], and is increased in people at higher risk for coronary heart disease. Table 3 shows the effect of supplementation of diet with the BYTP on atherogenic index in hypercholesterolemic mice. A significant decrease was seen in the atherogenic index of hypercholesterolemic mice fed high cholesterol diet supplemented with BYTP when compared with hypercholesterolemic controls (Table 3). No significant decrease was seen in the atherogenic index of hypercholesterolemic mice fed a normal diet without BYTP supplementation.

TABLE 3*

| Group | Atherogenic Index (AI) |
|---|---|
| Hyp mice fed hyp-BYTP diet | $0.80 \pm 0.08^a$ |
| Hyp mice fed hyp diet | $4.22 \pm 0.96^b$ |
| Hyp mice fed norm diet | $2.51 \pm 0.24^{ab}$ |
| Hyp mice fed norm-BYTP diet | $0.62 \pm 0.05^a$ |
| Norm mice fed norm-BYTP diet | $0.39 \pm 0.13^a$ |
| Norm mice fed norm diet | $1.74 \pm 0.35^a$ |

*Values: mean ± SEM, N = 10, hyp = hypercholesterolemic, BYTP = bitter yam therapeutic product, norm = normal. Each group with different letter subscripts are significantly different (p < 0.05).

7.2.5. Effects of Administration of BYTP on Lipid Peroxidation in Diabetic Rats Lipid peroxidation assays were conducted using the procedure of Tappel and Zalkin, *Arch Biochim Biophys*, 80: 333-336 (1959). Concentration of conjugated dienes in the liver was determined using the method of Hu et al., *J Nutr*, 119: 1574-1582 (1989).

Table 4 shows the effects of supplementation of diet with BYTP on thiobarbituric acid reactive substances (TBARS) in diabetic rats. The levels of conjugated dienes and TBARS in diabetic rats were significantly increased in relation to the normal group. Treatment with BYTP caused a significant decrease in kidney and liver conjugated dienes and TBARS levels, when compared to the diabetic and normal groups, thus reducing the undesired lipid peroxidation.

TABLE 4*

| Rat group | Conjugated dienes (μmole/g liver) | Liver TBARS (nmol/g liver) | Kidney TBARS (nmol/g kidney) |
|---|---|---|---|
| Normal | 0.495 ± 0.04$^b$ | 26.1 ± 2.9$^b$ | 85.3 ± 6.4$^{ab}$ |
| Diabetic | 0.582 ± 0.068$^c$ | 31.3 ± 2.2$^b$ | 106.7 ± 6.4$^b$ |
| Diabetic fed sapogenin extract | 0.416 ± 0.023$^a$ | 17.7 ± 1.1$^a$ | 59.7 ± 3.1$^a$ |
| Diabetic fed diosgenin | 0.428 ± 0.082$^a$ | 18.1 ± 2.1$^a$ | 61.7 ± 6.6$^a$ |
| Diabetic fed bitter yam | 0.438 ± 0.065$^a$ | 18.6 ± 2.9$^a$ | 77.1 ± 4.5$^a$ |
| Diabetic fed BYTP | 0.411 ± 0.015$^a$ | 18.0 ± 1.5$^a$ | 58.6 ± 2.7$^a$ |

*Values expressed as mean ± SEM. Figures in columns with different letter superscripts are significantly different ($p < 0.05$).

7.2.6. Effects of Administration of BYTP on Transaminases and Acid Phosphatase Activities of the Liver, Kidneys and Spleen in Diabetic Rats Tables 5-7 show the effect of the BYTP on transaminases and acid phosphatase in the liver, kidney and spleen. The activity of alanine transaminase of the liver was significantly increased in diabetic rats compared to normal rats. Treatment with the BYTP significantly lowered alanine transaminase activity towards the level found in normal rats. Aspartate transaminases and acid phosphatase activities were not affected by the induction of diabetes. Treatment of diabetic rats with the BYTP resulted in a significant decrease in aspartate transaminase activity compared to the normal and diabetic groups.

Table 5 shows the effect of BYTP on liver function, as evidenced by liver transaminases and acid phosphatase activities.

TABLE 5*

| Rat group | Alanine transaminase (mg pyr/min/mg protein × 10$^{-4}$) | Aspartate transaminase (mg pyr/min/mg protein × 10$^{-4}$) | Acid phosphatase (mg PNP/min/mg protein × 10$^{-5}$) |
|---|---|---|---|
| Normal | 16.9 ± 2.15$^a$ | 9.1 ± 1.5$^b$ | 16.2 ± 0.5$^a$ |
| Diabetic | 22.4 ± 4.14$^b$ | 10.4 ± 1.8$^b$ | 17.9 ± 0.5$^a$ |
| Diabetic fed sapogenin extract | 12.6 ± 1.80$^a$ | 8.5 ± 0.7$^{ab}$ | 17.9 ± 0.6$^a$ |
| Diabetic fed diosgenin | 14.1 ± 2.80$^a$ | 8.6 ± 0.7$^{ab}$ | 17.3 ± 0.9$^a$ |
| Diabetic fed bitter yam | 17.2 ± 1.80$^a$ | 7.3 ± 0.7$^a$ | 14.8 ± 0.8$^a$ |
| Diabetic fed BYTP | 13.2 ± 1.70$^a$ | 7.1 ± 0.7$^a$ | 13.9 ± 0.6$^a$ |

*Values expressed as mean ± SEM. Figures in same columns with different letter superscripts are significantly different ($p < 0.05$).

As can be seen from Table 5, BYTP was at least as effective, and in some instances more effective, in reducing alanine transaminase, aspartate transaminase and acid phosphatase activities in the liver compared to sapogenin extract, commercially available diosgenin, and Jamaican bitter yam.

Table 6 shows the effect of BYTP on kidney transaminases and acid phosphatase activities.

TABLE 6*

| Rat group | Alanine transaminase (mg pyr/min/mg protein × 10$^{-4}$) | Aspartate transaminase (mg pyr/min/mg protein × 10$^{-4}$) | Acid phosphatase (mg PNP/min/mg protein × 10$^{-5}$) |
|---|---|---|---|
| Normal | 6.0 ± 0.3$^a$ | 6.1 ± 0.3$^a$ | 27.8 ± 0.9$^a$ |
| Diabetic | 6.2 ± 0.8$^a$ | 6.1 ± 0.5$^a$ | 26.1 ± 2.9$^a$ |
| Diabetic fed sapogenin extract | 5.0 ± 0.3$^b$ | 5.3 ± 0.2$^b$ | 27.9 ± 1.0$^a$ |
| Diabetic fed diosgenin | 5.4 ± 0.5$^a$ | 5.5 ± 0.6$^{bc}$ | 27.3 ± 1.1$^a$ |
| Diabetic fed bitter yam | 7.6 ± 0.9$^c$ | 6.9 ± 0.5$^a$ | 26.3 ± 3.0$^a$ |
| Diabetic fed BYTP | 5.1 ± 0.5$^b$ | 5.3 ± 0.4$^b$ | 27.4 ± 0.9$^a$ |

*Values expressed as mean ± SEM. Figures in same columns with different letter superscripts are significantly different ($p < 0.05$)

Kidney acid phosphatase, alanine and aspartate transaminase activities were not significantly altered in diabetic rats compared to the normal rats. Diet supplementation with the BYTP significantly reduced the activities of the transaminases compared to the normal and diabetic control groups. Acid phosphatase activity was not altered by the BYTP supplementation.

As can be seen from Table 6, BYTP was at least as effective, and in some instances more effective, in reducing alanine transaminase, aspartate transaminase and acid phosphatase activities in the kidney compared to sapogenin extract, commercially available diosgenin, and Jamaican bitter yam.

Table 7 shows the effect of BYTP supplementation on spleen transaminase and acid phosphatase activities.

TABLE 7*

| Rat group | Alanine transaminase (mg pyr/min/mg protein × 10$^{-4}$) | Aspartate transaminase (mg pyr/min/mg protein × 10$^{-4}$) | Acid phosphatase (mg PNP/min/mg protein × 10$^{-5}$) |
|---|---|---|---|
| Normal | 9.7 ± 0.2$^{ab}$ | 7.5 ± 0.1$^a$ | 2.7 ± 0.3$^a$ |
| Diabetic | 13.9 ± 0.2$^a$ | 8.5 ± 0.4$^a$ | 3.9 ± 0.6$^a$ |
| Diabetic fed sapogenin extract | 8.4 ± 0.2$^{bc}$ | 6.9 ± 0.7$^{ab}$ | 7.0 ± 0.8$^b$ |
| Diabetic fed diosgenin | 10.7 ± 1.8$^{ab}$ | 7.1 ± 1.3$^{ab}$ | 9.0 ± 0.8$^b$ |
| Diabetic fed bitter yam | 6.9 ± 0.8$^c$ | 6.4 ± 0.3$^b$ | 3.2 ± 0.6$^a$ |
| Diabetic fed BYTP | 7.0 ± 0.2$^c$ | 6.2 ± 0.4$^b$ | 3.0 ± 0.5$^a$ |

*Values expressed as mean ± SEM. Figures in same columns with different letter superscripts are significantly different ($p < 0.05$).

Spleen acid phosphatase, alanine and aspartate transaminase activities were all increased in diabetic rats when compared to the normal group. Treatment with the BYTP resulted in significant decreases in the activities of the transaminases and acid phosphatase compared to the diabetic group, and in statistically significant decreases in the activities of the transaminases compared to the normal group.

As can be seen from Table 7, BYTP was at least as effective, and in some instances more effective, in reducing alanine transaminase, aspartate transaminase and acid phosphatase activities in the spleen compared to sapogenin extract, commercially available diosgenin, and Jamaican bitter yam.

7.2.7. Effect of Administration of BYTP on Intestinal Amylase Activity

Figure 5:
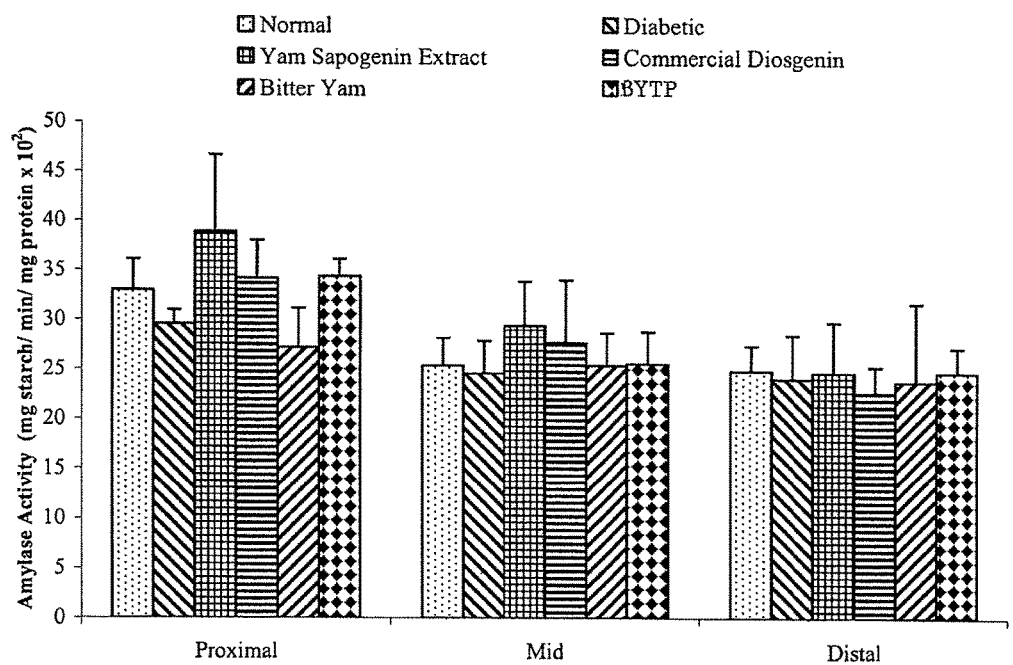
FIG. 5 is an illustration of the intestinal amylase activity in diabetic rats fed diet supplemented with Jamaican bitter yam therapeutic product (BYTP) and in control groups.

FIG. 5 shows the effect of BYTP on intestinal amylase activity. Intestinal amylase is an enzyme responsible for carbohydrate digestion. Amylase activity was determined by measuring the amount of starch hydrolyzed using the method of Wotton, Microanalysis in Medical Biochemistry, Churchill Ltd., Edinburgh, pp. 110-115. The activity of intestinal amylase was reduced in the proximal region in diabetic rats compared to normal rats. Supplementation of the diet with BYTP resulted in an increase in intestinal amylase activity when compared with the diabetic rats.

7.2.8. Effect of Administration of BYTP on Activities of Intestinal Lipases

Figure 6:
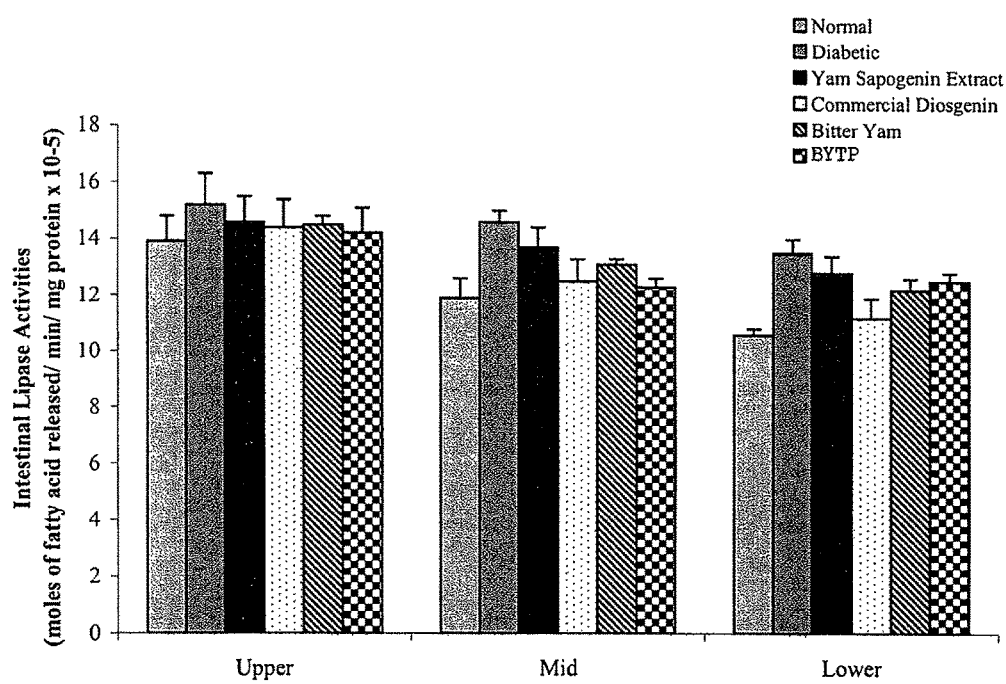
FIG. 6 is an illustration of the intestinal lipase activity in diabetic rats fed diet supplemented with Jamaican bitter yam therapeutic product (BYTP) and in control groups.

FIG. 6 shows the effect of BYTP on intestinal lipase activity. No significant differences were observed in intestinal lipase activity of the BYTP treated rats as compared with the diabetic control group in all regions of the intestine.

7.2.9. Effect of Administration of BYTP on Activities of Intestinal ATPases $Na^+/K^+$ and $Ca^+$ ATPase activities were measured by the amount of inorganic phosphate released following incubation with disodium ATP and cations for the appropriate ATPase (see Bonting et al., Sodium-potassium activated adenosinetriphosphatase and cation transport, in Membranes and Ion Transport I, Bittar (Ed.). Wiley-Interscience, N.Y., pp. 257-363 (1970); and Bonting et al., *Archives of Biochemistry and Biophysics* 101: 47-55 (1963)). The inorganic phosphate was determined by the method of Fiske and Subarow, *Journal of Biological Chemistry* 66: 375-400 (1925).

Table 8 shows the effect of BYTP on the activity of intestinal ATPases. Significant reductions in the activities of the ATPases in all sections of the intestines were seen in BYTP-treated diabetic rats when compared to untreated diabetic rats.

7.2.10 Effect of Administration of BYTP on Glucose-6-Phosphatase Activity

Table 9 shows the effect of BYTP on glucose-6-phosphatase activity in the liver and kidneys of rats fed diets supplemented with BYTP. The activity of glucose-6-phosphatase was significantly increased in the liver and kidney of the diabetic control rats when compared to the normal group. Supplementation of the diet with BYTP resulted in significant reductions in glucose-6-phosphatase activities of the liver and kidneys when compared with diabetic controls.

TABLE 9*

| Rat group | Liver | Kidney |
|---|---|---|
| | ($\mu$mole/min/mg protein $\times 10^{-2}$) | |
| Normal | $5.4 \pm 1.4^a$ | $6.4 \pm 1.3^a$ |
| Diabetic | $11.3 \pm 1.4^b$ | $13.9 \pm 0.8^b$ |
| Diabetic fed yam sapogenin extract | $7.6 \pm 1.9^a$ | $10.3 \pm 1.2^b$ |
| Diabetic fed diosgenin | $8.3 \pm 1.0^a$ | $11.0 \pm 2.0^b$ |
| Diabetic fed bitter yam | $7.7 \pm 2.3^a$ | $10.8 \pm 1.3^b$ |
| Diabetic fed BYTP | $7.0 \pm 1.1^a$ | $9.8 \pm 0.7^b$ |

*Values expressed as mean ± SEM. Figures in same columns with different letter superscripts are significantly different ($p < 0.05$).

7.2.11 Effect of Administration of BYTP on Intestinal Disaccharides

Figure 7:
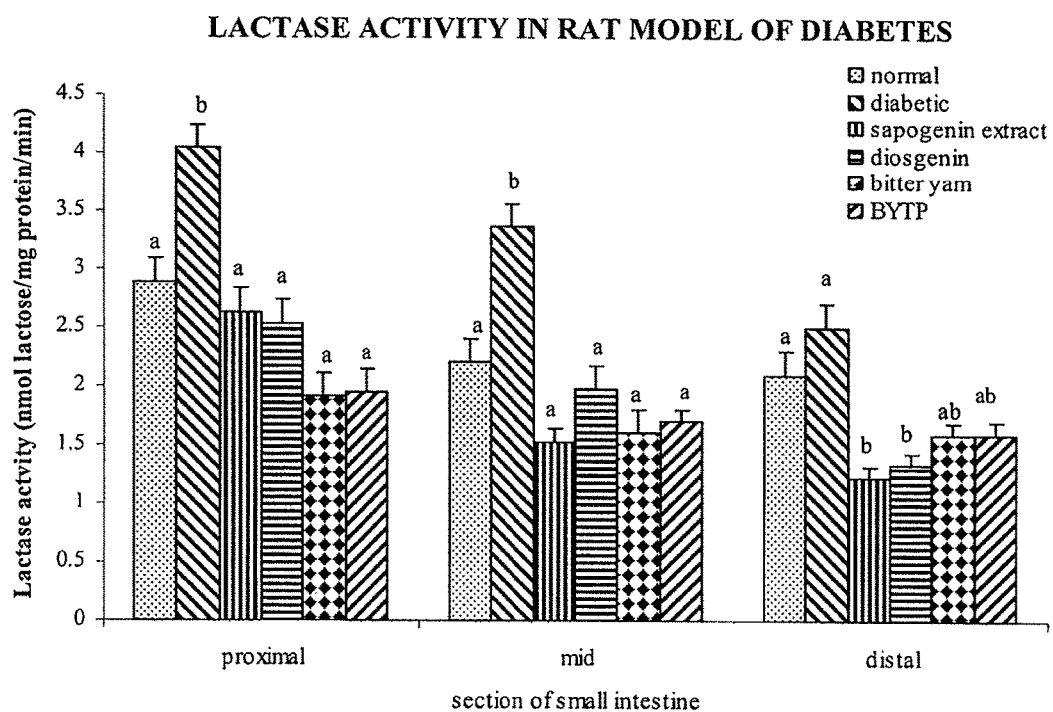
FIG. 7 is an illustration of the intestinal lactase activity in the intestines of diabetic rats fed diets supplemented with Jamaican bitter yam therapeutic product (BYTP) and in control groups.

As shown in FIG. 7, intestinal lactase activity is significantly increased in the proximal and mid regions of the small intestine in diabetic control rats when compared to the normal group. However, there is no less of an increase in the distal region of the intestine of the diabetic control group compared to the normal group. Treatment of diabetic rats with the BYTP resulted in a significant decrease in lactase activity in the proximal and mid regions of the small intestine. There were no significant changes in lactase activity of the rats fed diets with the BYTP supplementation, among the proximal, mid, and distal region of the small intestine.

TABLE 8*

Specific activity of ATPases from rat intestinal sections (nmol $P_i$/min/mg protein)

| ATPase | Normal | Diabetic | Diabetic fed yam sapogenin extract | Diabetic fed diosgenin | Diabetic fed bitter yam | Diabetic fed BYTP |
|---|---|---|---|---|---|---|
| $Na^+/K^+$ | | | | | | |
| Proximal | $23.5 \pm 0.5^a$ | $18.2 \pm 0.3^b$ | $14.3 \pm 0.2^c$ | $12.8 \pm 0.2^c$ | $12.9 \pm 0.2^c$ | $12.9 \pm 0.1^c$ |
| Mid | $19.5 \pm 0.4^a$ | $15.6 \pm 0.3^b$ | $11.1 \pm 0.2^c$ | $9.5 \pm 0.1^c$ | $9.9 \pm 0.3^c$ | $10.6 \pm 0.2^c$ |
| Distal | $14.5 \pm 0.2^a$ | $12.5 \pm 0.2^b$ | $8.2 \pm 0.1^c$ | $7.3 \pm 0.1^c$ | $7.3 \pm 0.1^c$ | $7.2 \pm 0.1^c$ |
| $Mg^{2+}$ | | | | | | |
| Proximal | $26.1 \pm 0.6^a$ | $26.6 \pm 0.3^a$ | $30.4 \pm 0.9^b$ | $27.8 \pm 0.5^a$ | $22.5 \pm 0.4^c$ | $22.7 \pm 0.4^C$ |
| Mid | $25.2 \pm 0.4^a$ | $20.8 \pm 0.6^b$ | $24.0 \pm 0.4^a$ | $22.1 \pm 0.4^b$ | $19.8 \pm 0.8^b$ | $20.4 \pm 0.4^b$ |
| Distal | $17.8 \pm 0.2^a$ | $13.9 \pm 0.3^b$ | $13.9 \pm 0.4^b$ | $16.4 \pm 0.6^a$ | $14.2 \pm 0.3^b$ | $13.9 \pm 0.4^b$ |
| $Ca^{2+}$ | | | | | | |
| Proximal | $34.9 \pm 0.7^a$ | $24.7 \pm 0.1^b$ | $24.5 \pm 0.6^b$ | $34.9 \pm 0.6^a$ | $15.8 \pm 0.5^c$ | $17.8 \pm 0.2^c$ |
| Mid | $22.7 \pm 0.7^a$ | $14.6 \pm 0.1^{bc}$ | $12.6 \pm 0.4^b$ | $17.1 \pm 0.4^c$ | $14.7 \pm 0.7^{bc}$ | $16.9 \pm 0.1^c$ |
| Distal | $20.2 \pm 0.8^a$ | $12.7 \pm 0.1^{bc}$ | $10.9 \pm 0.1^{bc}$ | $13.1 \pm 0.3^b$ | $8.9 \pm 0.1^c$ | $9.2 \pm 0.1^c$ |

*Values expressed as mean ± SEM. Figures in same columns with different letter superscripts are significantly different ($p < 0.05$).

As shown in Table 10, intestinal maltase activity was significantly increased in all regions in diabetic control rats when compared to the normal group. Supplementation of the diet with the BYTP resulted in significant decreases in maltase activity in all regions of the intestine when compared with the diabetic control group.

TABLE 10*

Specific activity of maltase from different sections of the rat intestine (nmol maltase/min/mg protein)

| Rat group | Upper | Mid | Distal |
|---|---|---|---|
| Normal | 20.0 ± 1.0[a] | 17.1 ± 1.1[a] | 15.5 ± 1.2[a] |
| Diabetic | 25.5 ± 1.7[b] | 21.5 ± 1.4[b] | 19.4 ± 2.1[b] |
| Diabetic fed sapogenin extract | 19.6 ± 1.2[a] | 16.2 ± 0.8[a] | 14.3 ± 1.3[a] |
| Diabetic fed diosgenin | 18.4 ± 1.2[a] | 17.1 ± 0.9[a] | 14.0 ± 1.0.[A] |
| Diabetic fed bitter yam | 20.6 ± 1.3[a] | 18.5 ± 1.3[a] | 17.1 ± 0.9[a] |
| Diabetic fed BYTP | 19.8 ± 1.0[a] | 17.6 ± 1.2[a] | 16.1 ± 1.4[a] |

*Values expressed as mean ± SEM. Figures in same columns with different letter superscripts are significantly different ($p < 0.05$).

Figure 8:
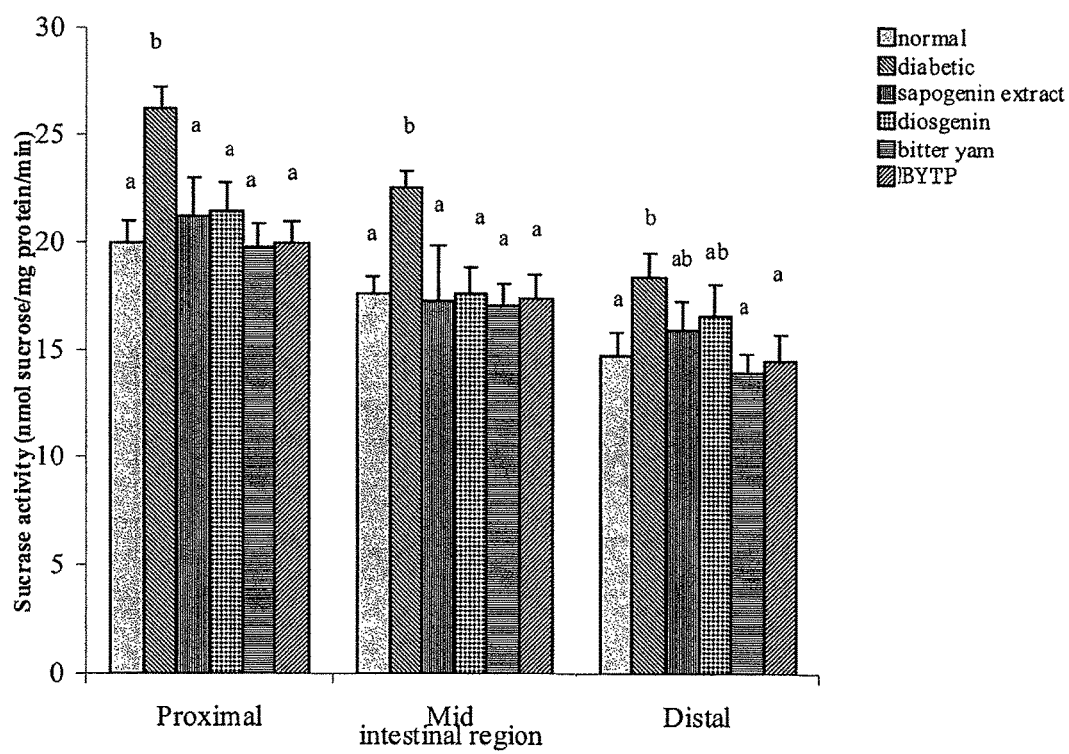
FIG. 8 is an illustration of intestinal sucrase activity in the intestines of diabetic rats fed diets supplemented with Jamaican bitter yam therapeutic product (BYTP) and in control groups.

As shown in FIG. 8, intestinal sucrase activity was significantly increased in all regions in diabetic control rats when compared to the normal group. Treatment with the BYTP resulted in a significant decrease in sucrase activity in all regions when compared with the diabetic group.

What is claimed is:

1. A composition for treating diabetes or hypercholesterolemia comprising an effective amount of solid Jamaican bitter yam therapeutic product, wherein said solid Jamaican bitter yam therapeutic product comprises fibers and saponins and less than about 0.1% tannins by weight and less than about 0.1% alkaloids by weight, wherein said solid Jamaican bitter yam therapeutic product is obtained by pulverizing Jamaican bitter yam into a powder and soaking the powder with a basic solution to substantially remove tannins, followed by filtration, and wherein said composition is in the form of a capsule, a tablet, a pill, a troch, a cream, a gel, or an emulsion.

2. The composition of claim 1, wherein the basic solution comprises sodium carbonate, sodium hydroxide, or potassium hydroxide.

3. The composition of claim 1, wherein the saponins comprise diosgenin.

4. The composition of claim 1, wherein the composition decreases blood glucose levels when administered to a diabetic subject.

5. The composition of claim 1, wherein the composition decreases total cholesterol levels when administered to a diabetic or hypercholesterolemic subject.

6. The composition of claim 1, wherein the solid Jamaican bitter yam therapeutic product further comprises one or more phenols.

7. The composition of claim 1, wherein the composition is substantially free of Jamaican bitter yam peel.

8. The composition of claim 1, wherein said solid Jamaican bitter yam therapeutic product is obtained by: (a) providing Jamaican bitter yam; (b) pulverizing the Jamaican bitter yam into a powder; and (c) removing tannins and alkaloids from the powder to provide a substantially tannin-free and substantially alkaloid-free composition.

9. The composition of claim 8, wherein the tannins in the powder are removed by soaking the powder in the basic solution.

10. The composition of claim 8, wherein the alkaloids in the powder are removed by chromatographic separation.

11. The composition of claim 8, wherein the method further comprises drying the Jamaican bitter yam prior to pulverizing the Jamaican bitter yam.

12. The composition of claim 11, wherein the method further comprises removing the peel from the Jamaican bitter yam prior to drying the Jamaican bitter yam.

13. The composition of claim 1, wherein said solid Jamaican bitter yam therapeutic product is obtained by: (a) providing Jamaican bitter yam; (b) drying and grinding the Jamaican bitter yam into a powder; (c) removing tannins from the powder by soaking the powder in the basic solution and removing the filtrate to provide a substantially tannin-free residue; (d) soaking the substantially tannin-free residue in a solvent to provide a substantially tannin-free solution; (e) removing all solid components from the solution; (f) removing alkaloids from the solution by chromatographic separation to provide a substantially alkaloid-free and substantially tannin-free solution; (g) removing the solvent from the substantially alkaloid-free and substantially tannin-free solution to provide a substantially alkaloid-free and substantially tannin-free solid; and (h) combining the substantially alkaloid-free and substantially tannin-free solid with the solid components from step (e) to provide the therapeutic product.

14. The composition of claim 13, wherein the solvent is methanol.

* * * * *